US012700090B2

(12) United States Patent
Nakamura et al.

(10) Patent No.: US 12,700,090 B2
(45) Date of Patent: Aug. 4, 2026

(54) INFORMATION MANAGEMENT APPARATUS TO ACQUIRE MEDICAL IMAGE FOR FINDING REMARK RELATED TO REGION OF INTEREST INCLUDING ABNORMAL AREA AND NON-TRANSITORY COMPUTER-READABLE STORAGE MEDIUM

(71) Applicant: FUJIFILM Corporation, Tokyo (JP)

(72) Inventors: Keigo Nakamura, Minato-ku (JP); Jun Masumoto, Minato-ku (JP); Yuya Hamaguchi, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

(21) Appl. No.: 18/460,712

(22) Filed: Sep. 5, 2023

(65) Prior Publication Data

US 2023/0410305 A1 Dec. 21, 2023

Related U.S. Application Data

(63) Continuation of application No. PCT/JP2022/002461, filed on Jan. 24, 2022.

(30) Foreign Application Priority Data

Mar. 19, 2021 (JP) ................................. 2021-046613
Dec. 22, 2021 (JP) ................................. 2021-208718

(51) Int. Cl.
*G06T 7/00* (2017.01)
*G16H 30/20* (2018.01)
(Continued)

(52) U.S. Cl.
CPC ........... *G06T 7/0012* (2013.01); *G16H 30/20* (2018.01); *G06N 3/08* (2013.01);
(Continued)

(58) Field of Classification Search
None
See application file for complete search history.

(56) References Cited

U.S. PATENT DOCUMENTS 9,117,009 B2 8/2015 Iizuka et al.
2007/0237377 A1 10/2007 Oosawa
(Continued)

FOREIGN PATENT DOCUMENTS

JP H0731591 2/1995
JP H07323024 12/1995
(Continued)

OTHER PUBLICATIONS

"Search Report of Europe Counterpart Application", issued on Aug. 1, 2024, p. 1-p. 8.
(Continued)

*Primary Examiner* — Haris Sabah
(74) *Attorney, Agent, or Firm* — JCIPRNET

(57) ABSTRACT

A processor acquires at least one finding about at least one region of interest included in a medical image, derives correspondence information in which the at least one finding and medical image information about the region of interest are associated with each other, and registers the correspondence information in a database.

19 Claims, 13 Drawing Sheets

(51) Int. Cl.

| | | |
|---|---|---|
| *G06N 3/08* | (2023.01) | |
| *G06V 10/70* | (2022.01) | |
| *G06V 10/75* | (2022.01) | |

(52) U.S. Cl.

CPC .... *G06T 2207/30004* (2013.01); *G06V 10/70* (2022.01); *G06V 10/75* (2022.01)

(56)     References Cited

U.S. PATENT DOCUMENTS

| 2010/0189366 | A1 | | 7/2010 | Iizuka et al. | |
|---|---|---|---|---|---|
| 2012/0134555 | A1 | * | 5/2012 | Iizuka | G16H 30/20 |
| | | | | | 382/128 |
| 2017/0091949 | A1 | | 3/2017 | Akasaka et al. | |
| 2018/0089371 | A1 | * | 3/2018 | Matsuki | G06F 16/51 |
| 2018/0177446 | A1 | * | 6/2018 | Okabe | A61B 5/163 |
| 2018/0286503 | A1 | | 10/2018 | Sevenster | |
| 2019/0139218 | A1 | * | 5/2019 | Song | G06F 40/10 |
| 2019/0139642 | A1 | | 5/2019 | Roberge et al. | |
| 2019/0267132 | A1 | * | 8/2019 | Fuchigami | G06T 11/60 |
| 2019/0279751 | A1 | | 9/2019 | Nakamura et al. | |
| 2020/0193595 | A1 | * | 6/2020 | Iwamura | G16H 10/60 |

FOREIGN PATENT DOCUMENTS

| JP | 2007305107 | 11/2007 |
|---|---|---|
| JP | 2009110485 | 5/2009 |
| JP | 2011118543 | 6/2011 |
| JP | 2016040688 | 3/2016 |
| JP | 2017068380 | 4/2017 |
| JP | 2018534029 | 11/2018 |
| JP | 2019153250 | 9/2019 |
| WO | 2009041586 | 4/2009 |

OTHER PUBLICATIONS

"International Search Report (Form PCT/ISA/210) of PCT/JP2022/002461", mailed on Apr. 5, 2022, with English translation thereof, pp. 1-5.

"Written Opinion of the International Searching Authority (Form PCT/ISA/237) of PCT/JP2022/002461", mailed on Apr. 5, 2022, with English translation thereof, pp. 1-9.

"Office Action of Japan Counterpart Application", issued on Aug. 26, 2025, with English translation thereof, p. 1-p. 9.

"Notice of Reasons for Refusal of Japan Counterpart Application", issued on Feb. 3, 2026, with English translation thereof, p. 1-p. 9.

"Decision of Refusal of Japan Counterpart Application", issued on May 19, 2026, with English translation thereof, p. 1-p. 6.

* cited by examiner

20

INFORMATION MANAGEMENT APPARATUS

21
INFORMATION ACQUISITION UNIT

22
FIRST ANALYSIS UNIT

23
SECOND ANALYSIS UNIT

24
CORRESPONDENCE INFORMATION DERIVING UNIT

FIG. 7

| AREA | DISORDER TYPE | DISORDER NAME | DISORDER FEATURE 1 | DISORDER FEATURE 2 | DISORDER FEATURE 3 | ANATOMICAL LEVEL INFORMATION | SIZE LEVEL INFORMATION | MEDICAL IMAGE INFORMATION | FINDING REMARK GENERATION INFORMATION |
|---|---|---|---|---|---|---|---|---|---|
| LUNG | NODULAR TYPE | LUNG ADENOCARCINOMA | | | | LUNG SEGMENTS (S1 TO S8) | LENGTH | ☐☐ ☐☐ | <NLP> |
| | DIFFUSE TYPE | INTERSTITIAL PNEUMONIA | GROUND-GLASS OPACITY | ADHESION TO CHEST WALL | INTERIOR VOMICA | | | ☐ ☐ | <NLP> |
| CHEST AND ABDOMEN | | LYMPH NODE ENLARGEMENT | | | | ARMPIT, MEDIASTINUM, ABDOMEN | BREATH | ☐ ☐ | <TEMPLATE> |
| | NODULAR TYPE | CYST | LOW ABSORPTION | | | | SMALL | ☐ ☐ | <TEMPLATE> |
| | | HEPATOMA | Washout | VENOUS PHASE DEEP DYEING | | | | ☐☐ ☐ | <NLP> |
| LIVER | DIFFUSE TYPE | FATTY LIVER | LOW SIGNAL | | | | | ☐ ☐ | <NLP> |
| | | HEPATIC CIRRHOSIS | IRREGULAR | | | | | ☐ ☐ | <TEMPLATE> |
| | OTHERS | POST-OPERATION | RIGHT LOBE REMOVED | | | | | ☐☐ ☐ | <TEMPLATE> |
| HEAD | NODULAR TYPE | GLIOMA | EDEMA PRESENT | DEEP DYEING PRESENT | UNCLEAR MARGIN | | | ☐ ☐ | <TEMPLATE> |
| | STRUCTURAL ANOMALY | DEMENTIA | ATROPHY OF HIPPOCAMPUS | | | | | ☐☐ ☐ | <TEMPLATE> |

| AREA | DISORDER TYPE | DISORDER NAME | DISORDER FEATURE 1 | DISORDER FEATURE 2 | DISORDER FEATURE 3 | ANATOMICAL LEVEL INFORMATION | SIZE LEVEL INFORMATION | MEDICAL IMAGE INFORMATION | FINDING REMARK GENERATION INFORMATION |
|---|---|---|---|---|---|---|---|---|---|
| LUNG | NODULAR TYPE | LUNG ADENOCARCINOMA | | | | LUNG SEGMENTS (S1 TO S8) | LENGTH | □ □ □ | <NLP> |
| | DIFFUSE TYPE | INTERSTITIAL PNEUMONIA | GROUND-GLASS OPACITY | ADHESION TO CHEST WALL | INTERIOR VOMICA | | | □ □ □ / □ | <NLP> |
| CHEST AND ABDOMEN | | LYMPH NODE ENLARGEMENT | | | | ARMPIT, MEDIASTINUM, ABDOMEN | BREATH | □ □ | <TEMPLATE> |
| LIVER | NODULAR TYPE | CYST | LOW ABSORPTION | | | | SMALL | □ □ □ | <TEMPLATE> |
| | | HEPATOMA | Washout | VENOUS PHASE DEEP DYEING | | | | □ □ □ □ | <NLP> |
| | DIFFUSE TYPE | FATTY LIVER | LOW SIGNAL | | | | | □ □ □ | <NLP> |
| | | HEPATIC CIRRHOSIS | IRREGULAR | | | | | □ □ □ | <TEMPLATE> |
| | OTHERS | POST-OPERATION | RIGHT LOBE REMOVED | | | | | □ □ □ | <TEMPLATE> |
| HEAD | NODULAR TYPE | GLIOMA | EDEMA PRESENT | DEEP DYEING PRESENT | UNCLEAR MARGIN | | | □ □ | <TEMPLATE> |
| | STRUCTURAL ANOMALY | DEMENTIA | ATROPHY OF HIPPOCAMPUS | | | | | □ □ □ □ | <TEMPLATE> |

7A

INFORMATION MANAGEMENT APPARATUS TO ACQUIRE MEDICAL IMAGE FOR FINDING REMARK RELATED TO REGION OF INTEREST INCLUDING ABNORMAL AREA AND NON-TRANSITORY COMPUTER-READABLE STORAGE MEDIUM

CROSS-REFERENCE TO RELATED APPLICATIONS

The present application is a Continuation of PCT International Application No. PCT/JP2022/002461, filed on Jan. 24, 2022, which claims priority to Japanese Patent Application No. 2021-046613, filed on Mar. 19, 2021 and Japanese Patent Application No. 2021-208718, filed on Dec. 22, 2021. Each application above is hereby expressly incorporated by reference, in its entirety, into the present application.

BACKGROUND

Technical Field

The present disclosure relates to an information management apparatus, an information management method, an information management program, an information processing apparatus, an information processing method, and an information processing program.

Related Art

The recent advancement of medical apparatuses including CT (Computed Tomography) apparatuses and MRI (Magnetic Resonance Imaging) apparatuses allows image-based diagnoses using high-resolution medical images having higher quality. Specifically, image-based diagnoses using CT images, MRI images, and the like allow highly accurate identification of a lesion region, and this facilitates appropriate treatment based on the result of identification.

The practice of analyzing a medical image with CAD (Computer-Aided Diagnosis) using a trained model that has been trained with, for example, deep learning and detecting the properties including the shape, density, position, and size of an abnormal shadow such as a lesion included in the medical image is being done. The medical image and the result of analysis are transmitted to a terminal of an interpreting doctor who interprets the medical image. The interpreting doctor interprets the medical image with reference to the transmitted medical image and result of analysis and creates an interpretation report.

With the advancement in performance of CT apparatuses and MRI apparatuses described above, the number of medical images that are to be interpreted is increasing. To reduce effort made by interpreting doctors to perform interpretation work, various techniques for supporting creation of medical documents such as interpretation reports have been proposed. For example, a technique has been proposed in which the coordinates of a location at which an abnormality is found in a medical image are obtained, an organ and an area, in the image, pointed by the specified coordinates are sought from data of regions obtained by dividing the image into areas, and the names of the organ and the area in which the abnormality is found and the name of a disorder observed in the organ and the area are output (see JP1995-323024A (JP-H07-323024A)). Further, a technique has been proposed in which regions of interest that are put into the same group are identified from a plurality of regions of interest in a medical image and findings from the individual regions of interest and a finding common to the regions of interest included in the group are input to thereby efficiently create an interpretation report (see JP2017-068380A).

A large number of medical images and a large number of medical documents such as interpretation reports related to the medical images are saved in association with each other. To utilize later the large number of saved medical images and medical documents and findings about regions of interest included in the medical images, efficient management is desired.

SUMMARY OF THE INVENTION

The present disclosure has been made in view of the above-described circumstances, and an object thereof is to allow efficient management of a large number of medical images and findings on the medical images.

An information management apparatus according to the present disclosure includes: at least one processor, the processor being configured to acquire at least one finding about at least one region of interest included in a medical image, derive correspondence information in which the at least one finding and medical image information about the region of interest are associated with each other, and register the correspondence information in a database.

In the information management apparatus according to the present disclosure, the processor may be configured to acquire findings, each of which is the finding, from a plurality of medical images respectively, and derive the correspondence information in which each of the findings and a related one of pieces of medical image information, each of which is the medical image information, are associated with each other.

In the information management apparatus according to the present disclosure, the medical image information may include a local image of the region of interest in the medical image.

In the information management apparatus according to the present disclosure, the medical image information may include a feature value that indicates a feature of the region of interest in the medical image.

In the information management apparatus according to the present disclosure, the medical image information may include the medical image and positional information that indicates a position of the region of interest in the medical image.

In the information management apparatus according to the present disclosure, the processor may be configured to acquire a medical document associated with the medical image, and acquire the finding by identifying from the medical document, a finding about the region of interest included in the medical image.

In the information management apparatus according to the present disclosure, the processor may be configured to, when the region of interest includes an abnormal area, derive correspondence information in which the finding and the medical image information are associated with each other on a per-type-of-abnormal-area basis.

In the information management apparatus according to the present disclosure, the processor may be configured to, when the region of interest includes a normal area, derive correspondence information in which the finding and the medical image information are associated with each other on a per-type-of-normal-area basis.

In the information management apparatus according to the present disclosure, the finding may include a property of the region of interest.

In the information management apparatus according to the present disclosure, the finding may include anatomical level information that indicates a level of an anatomical segment of an organ that includes the region of interest.

In the information management apparatus according to the present disclosure, the finding may include size information that indicates at least one of a direction of measurement or a size level of a size of the region of interest.

In the information management apparatus according to the present disclosure, the finding may include at least one of a focal finding or a nonfocal finding.

In the information management apparatus according to the present disclosure, the processor may be configured to derive the correspondence information in which the finding and a generation method for medical information that includes the finding are further associated with each other.

An information processing apparatus according to the present disclosure includes: at least one processor, the processor being configured to acquire a target medical image that is a generation target of medical information, identify a target region of interest included in the target medical image, and identify a finding corresponding to medical image information that is about the target region of interest with reference to a database in which a plurality of pieces of correspondence information in each of which a finding and medical image information about a region of interest among various regions of interest included in a medical image among various medical images are associated with each other are registered.

In the information processing apparatus according to the present disclosure, the database may be created by registering correspondence information derived by the information management apparatus according to the present disclosure.

In the information processing apparatus according to the present disclosure, the processor may be configured to identify the finding that is related to a change from a healthy state of the target region of interest, with reference to the correspondence information.

In the information processing apparatus according to the present disclosure, the finding may indicate a focal finding or may indicate a nonfocal finding.

In the information processing apparatus according to the present disclosure, the processor may be configured to further generate medical information that includes the identified finding.

In the information processing apparatus according to the present disclosure, the correspondence information may be information in which the finding and a generation method for medical information that includes the finding are associated with each other, and the processor may be configured to identify a generation method for the medical information about the target region of interest with reference to the database, and derive the medical information that includes the identified finding on the basis of the identified generation method.

In the information processing apparatus according to the present disclosure, the medical information may be a medical document that includes the finding.

In the information processing apparatus according to the present disclosure, the processor may be configured to derive a plurality of medical documents each of which is the medical document.

In this case, the processor may be configured to display the plurality of medical documents.

In this case, the processor may be configured to display the plurality of medical documents so as to allow selection of at least one medical document from among the plurality of medical documents.

An information management method according to the present disclosure includes: acquiring at least one finding about at least one region of interest included in a medical image;

deriving correspondence information in which the at least one finding and medical image information about the region of interest are associated with each other; and registering the correspondence information in a database.

An information processing method according to the present disclosure includes: acquiring a target medical image that is a generation target of medical information;

identifying a target region of interest included in the target medical image; and identifying a finding corresponding to medical image information that is about the target region of interest with reference to a database in which a plurality of pieces of correspondence information in each of which a finding and medical image information about a region of interest among various regions of interest included in a medical image among various medical images are associated with each other are registered.

The information management method and the information processing method according to the present disclosure may be provided as programs for causing the computer to perform the methods.

According to the present disclosure, a medical document having content that accurately indicates the condition of a patient can be generated.

BRIEF DESCRIPTION OF THE DRAWINGS

FIG. 7 is a diagram illustrating an example of a management DB;

FIG. 14 is a diagram illustrating another example of the management DB.

DETAILED DESCRIPTION

Hereinafter, an embodiment of the present disclosure will be described with reference to the drawings. First, the configuration of a medical information system 1 to which an information management apparatus and an information processing apparatus according to the present embodiment are applied will be described.

Figure 1:
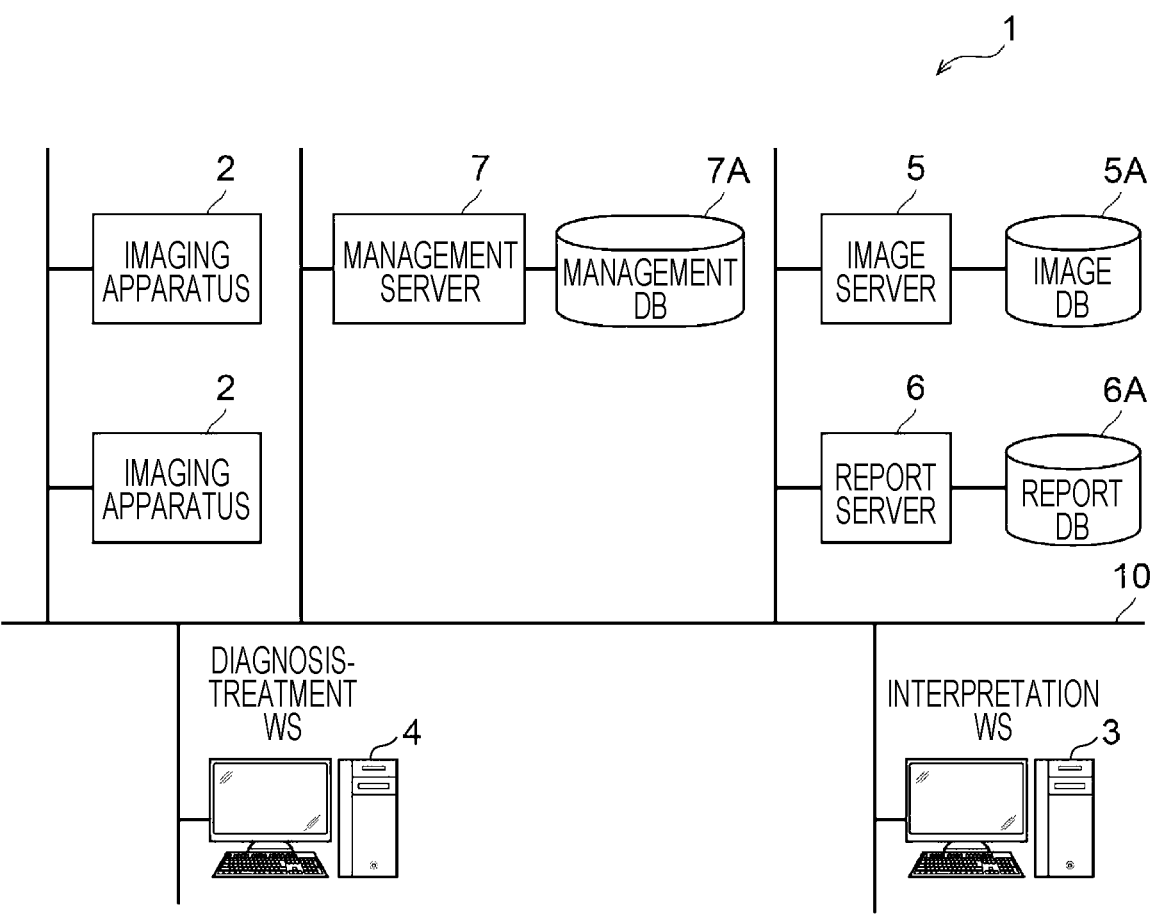
FIG. 1 is a diagram illustrating an example schematic configuration of a medical information system to which an information management apparatus and an information processing apparatus according to the present embodiment are applied.

FIG. 1 is diagram illustrating the schematic configuration of the medical information system 1. The medical information system 1 illustrated in FIG. 1 is a system for, on the basis of an examination order made by a doctor of a diagnosis-treatment department using a publicly known ordering system, imaging an examination target area of a patient who is a photographic subject, storing a medical image acquired by imaging, allowing an interpreting doctor to interpret the medical image and create an interpretation report, and allowing the doctor of the diagnosis-treatment department who has made the order to view the interpretation report and observe in detail the medical image that is an interpretation target.

As illustrated in FIG. 1, the medical information system 1 includes a plurality of imaging apparatuses 2, a plurality of interpretation WSs (workstations) 3 that are interpretation terminals, a diagnosis-treatment WS 4, an image server 5, an image DB (database) 5A, a report server 6, a report DB (database) 6A, a management server 7, and a management DB (database) 7A, which are connected to each other via a wired or wireless network 10 so as to be capable of communicating with each other.

Each of the apparatuses is a computer in which an application program for causing the apparatus to function as a configuration element of the medical information system 1 is installed. The application program is recorded to a recording medium, such as a DVD (Digital Versatile Disc) or a CD-ROM (Compact Disc Read-Only Memory) and distributed, and is installed in the computer from the recording medium. Alternatively, the application program is stored in a storage device of a server computer connected to the network 10 or in a network storage so as to be externally accessible, and in response to a request, downloaded to and installed in the computer.

The imaging apparatus 2 is an apparatus (modality) that images an area that is a diagnosis target of a patient to thereby generate a medical image that shows the diagnosis target area. Specifically, the imaging apparatus 2 is, for example, a plain X-ray imaging apparatus, a CT apparatus, an MRI apparatus, or a PET (Positron Emission Tomography) apparatus. The medical image generated by the imaging apparatus 2 is transmitted to the image server 5 and saved in the image DB 5A.

The interpretation WS 3 is a computer used by, for example, an interpreting doctor of a radiology department to, for example, interpret a medical image and create an interpretation report, and includes an information processing apparatus according to the present embodiment (which will be described in detail below). The interpretation WS 3 makes a request to view a medical image to the image server 5, performs various types of image processing for the medical image received from the image server 5, displays the medical image, and accepts input of a finding remark on the medical image. The interpretation WS 3 performs an analysis process for the medical image, supports creation of an interpretation report based on the result of analysis, makes a request to register the interpretation report and a request to view an interpretation report to the report server 6, and displays the interpretation report received from the report server 6. These processes are performed by the interpretation WS 3 executing a software program for the processes.

The diagnosis-treatment WS 4 is a computer used by, for example, a doctor of a diagnosis-treatment department to, for example, observe an image in detail, view an interpretation report, and create an electronic medical chart, and includes a processing device, a display device such as a display, and an input device including a keyboard and a mouse. The diagnosis-treatment WS 4 makes a request to view an image to the image server 5, displays the image received from the image server 5, makes a request to view an interpretation report to the report server 6, and displays the interpretation report received from the report server 6. These processes are performed by the diagnosis-treatment WS 4 executing a software program for the processes.

The image server 5 is a general-purpose computer in which a software program for providing a database management system (DBMS) function is installed. The image server 5 includes a storage in which the image DB 5A is set up. This storage may be a hard disk apparatus that is connected to the image server 5 via a data bus or may be an NAS (Network Attached Storage) that is connected to the network 10 or a disk device that is connected to an SAN (Storage Area Network). When accepting a request from the imaging apparatus 2 to register a medical image, the image server 5 puts the medical image into a database format and registers the medical image in the image DB 5A.

In the image DB 5A, image data of a medical image acquired by the imaging apparatus 2 and accessory information are registered. The accessory information includes, for example, an image ID (identification) for identifying the individual medical image, a patient ID for identifying the patient, an examination ID for identifying the examination, a unique ID (UID: unique identification) assigned on a medical image by medical image basis, the examination date and the examination time when the medical image is generated, the type of the imaging apparatus used in the examination for acquiring the medical image, patient information including the name, age, and sex of the patient, the examined area (imaged area), imaging information (the imaging protocol, the imaging sequence, the imaging method, imaging conditions, use of a contrast medium, and so on), and the series numbers or collection numbers when a plurality of medical images are acquired in a single examination.

When receiving a viewing request from the interpretation WS 3 and the diagnosis-treatment WS 4 via the network 10, the image server 5 retrieves a medical image registered in the image DB 5A and transmits the retrieved medical image to the interpretation WS 3 or the diagnosis-treatment WS 4 that has made the request.

In the report server 6, a software program that provides a database management system function to general-purpose computers is installed. When accepting a request to register an interpretation report from the interpretation WS 3, the report server 6 puts the interpretation report into a database format and registers the interpretation report in the report DB 6A.

In the report DB 6A, a large number of interpretation reports including finding remarks and created by interpreting doctors using the interpretation WS 3 are registered. Each of the interpretation reports may include, for example, a medical image that is an interpretation target, an image ID for identifying the medical image, an interpreting doctor ID for identifying the interpreting doctor who has made the interpretation, the name of a lesion, positional information of the lesion, and the properties of the lesion. In the present embodiment, in the report DB 6A, an interpretation report and one or more medical images on which the interpretation report is created are registered in association with each other. The interpretation report is an example of a medical document of the present disclosure.

When receiving a request to view an interpretation report from the interpretation WS 3 or the diagnosis-treatment WS 4 via the network 10, the report server 6 retrieves the interpretation report registered in the report DB 6A and transmits the retrieved interpretation report to the interpretation WS 3 or the diagnosis-treatment WS 4 that has made the request.

The management server 7 is a general-purpose computer in which a software program for providing a database management system function is installed. The management server 7 includes an information management apparatus according to the present embodiment (which will be described in detail below). The management server 7 registers correspondence information derived as described below in the management DB 7A.

The network 10 is a wired or wireless local area network that connects various apparatuses in the hospital to each other. When the interpretation WS 3 is installed in another hospital or a clinic, the network 10 may be configured so as to connect local area networks in the respective hospitals to each other via the Internet or a dedicated line.

Figure 2:
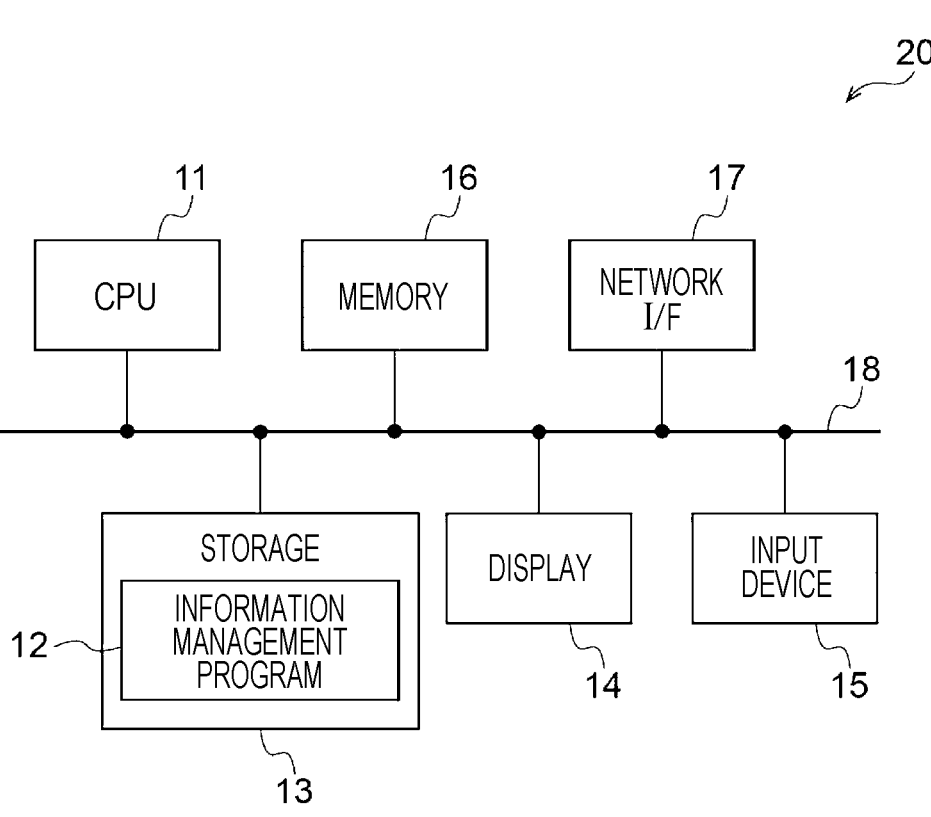
FIG. 2 is a block diagram illustrating an example hardware configuration of the information management apparatus according to the present embodiment.

Next, an information management apparatus 20 according to the present embodiment included in the management server 7 will be described. First, the hardware configuration of the information management apparatus 20 according to the present embodiment will be described with reference to FIG. 2. As illustrated in FIG. 2, the information management apparatus 20 includes a CPU (central processing unit) 11, a nonvolatile storage 13, and a memory 16 that is a temporary storage area. The information management apparatus 20 further includes a display 14, which is, for example, a liquid crystal display, an input device 15 including a keyboard and a pointing device such as a mouse, and a network I/F (interface) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is implemented as, for example, an HDD (hard disk drive), an SSD (solid state drive), and a flash memory. In the storage 13 that is a storage medium, an information management program 12 is stored. The CPU 11 reads the information management program 12 from the storage 13, loads the information management program 12 to the memory 16, and executes the loaded information management program 12.

Figures 3, 4:
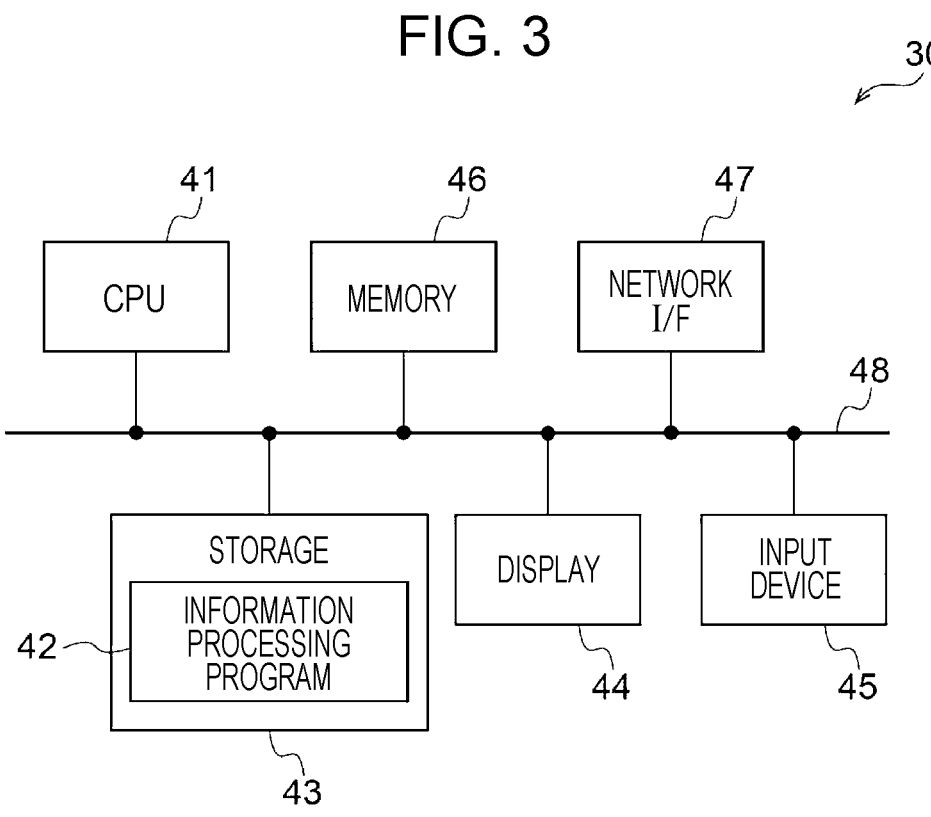
FIG. 3 is a block diagram illustrating an example hardware configuration of the information processing apparatus according to the present embodiment.
FIG. 4 is a block diagram illustrating an example functional configuration of the information management apparatus according to the present embodiment.

Next, an information processing apparatus 30 according to the present embodiment included in the interpretation WS 3 will be described. First, the hardware configuration of the information processing apparatus 30 according to the present embodiment will be described with reference to FIG. 3. As illustrated in FIG. 3, the information processing apparatus 30 includes a CPU 41, a nonvolatile storage 43, and a memory 46 that is a temporary storage area. The information processing apparatus 30 further includes a display 44, which is, for example, a liquid crystal display, an input device 45 including a keyboard and a pointing device such as a mouse, and a network I/F 47 connected to the network 10. The CPU 41, the storage 43, the display 44, the input device 45, the memory 46, and the network I/F 47 are connected to a bus 48. The CPU 41 is an example of a processor in the present disclosure.

The storage 43 is implemented as, for example, an HDD, an SSD, or a flash memory similarly to the storage 13. In the storage 43 that is a storage medium, an information processing program 42 is stored. The CPU 41 reads the information processing program 42 from the storage 43, loads the information processing program 42 to the memory 46, and executes the loaded information processing program 42.

Next, the functional configuration of the information management apparatus according to the present embodiment included in the management server 7 will be described. FIG. 4 is a diagram illustrating the functional configuration of the information management apparatus according to the present embodiment. As illustrated in FIG. 4, the information management apparatus 20 includes an information acquisition unit 21, a first analysis unit 22, a second analysis unit 23, and a correspondence information deriving unit 24. When the CPU 11 executes the information management program 12, the CPU 11 functions as the information acquisition unit 21, the first analysis unit 22, the second analysis unit 23, and the correspondence information deriving unit 24.

Figure 5:
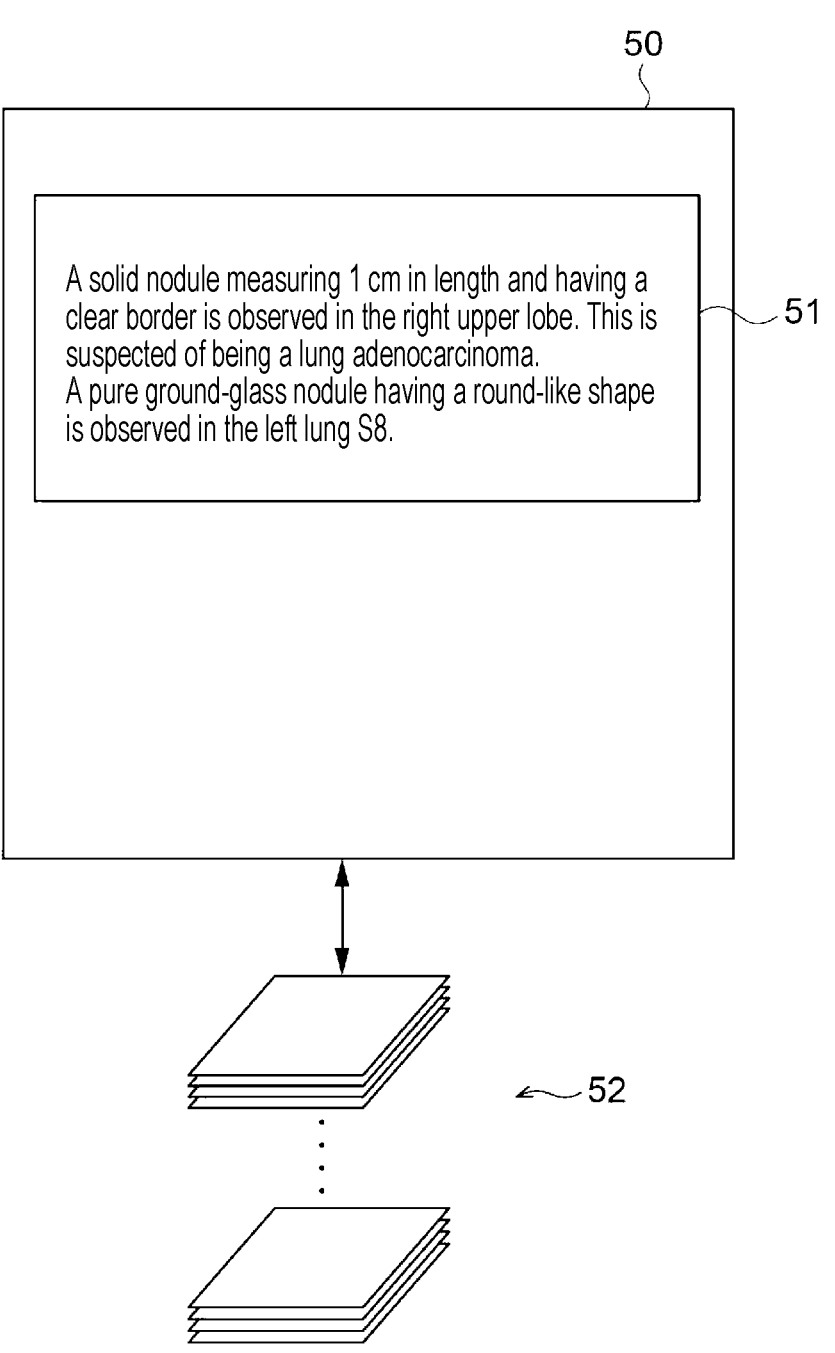
FIG. 5 is a diagram illustrating an example interpretation report.

The information acquisition unit 21 acquires a medical image and an interpretation report associated with the medical image from the image server 5 and the report server 6 respectively via the network I/F 17. FIG. 5 is a diagram illustrating an example interpretation report. As illustrated in FIG. 5, an interpretation report 50 includes a finding remark 51. The finding remark 51 says "A solid nodule measuring 1 cm in length and having a clear border is observed in the right upper lobe. This is suspected of being a lung adenocarcinoma. A pure ground-glass nodule having a round-like shape is observed in the left lung S8". As illustrated in FIG. 5, the interpretation report 50 is associated with a medical image 52 on which the interpretation report 50 is created. More specifically, among a plurality of tomographic images included in the medical image, the interpretation report 50 is associated with a tomographic image including a region of interest for which findings are recorded in the interpretation report 50.

The first analysis unit 22 analyzes the finding remark 51 included in the interpretation report 50 to thereby acquire findings about the region of interest included in the medical image 52. Specifically, the first analysis unit 22 analyzes a character string included in the interpretation report by using a natural language processing technique to thereby extract from the interpretation report, findings about the region of interest that are included in the interpretation report. Specific examples of the findings include the position and type of the region of interest, and when the region of interest includes an abnormal area, the disorder type, the disorder name, disorder features, and the size. The finding remark 51 also includes findings observed when the region of interest includes a normal area, and therefore, the first analysis unit 22 acquires the findings observed when the region of interest includes a normal area. A finding remark including a finding about a normal area is, for example, "Features of A are observed, and therefore, the area is normal". Here, "A" is a finding observed when the area is normal.

In the interpretation report, the properties of the region of interest are recorded. For example, when the region of interest is included in the lung, the properties about a plurality of items including the type of absorption value (solid or pure ground-glass), the presence or absence of a spicula, the presence or absence of a calcification, the presence or absence of a vomica, the presence or absence of pleural indentation, the presence or absence of pleural contact, and the presence or absence of a pleural invasion are recorded. The first analysis unit 22 acquires the properties of the region of interest recorded in the interpretation report as findings.

Depending on the region of interest, the direction of measurement of the size may be specified in advance. For example, in a case of a lung cancer, the length of the lung cancer is recorded in the interpretation report as the size, and in a case of a lymphadenoma, the breath of the lymphadenoma is recorded in the interpretation report as the size. The size of a cyst is not important, and only information about, for example, whether the cyst is small or large is recorded in the interpretation report. Therefore, the first analysis unit 22 acquires as a finding, size information that includes the direction of measurement of the size included in the interpretation report and information indicating whether the size is small or large (for example, small, very small, or large).

In the interpretation report, the name of an organ that includes the region of interest is recorded as a finding, and upon the recording, the anatomical segment of the organ is recorded. For example, the lung can be divided into anatomical segments of the left lung and the right lung or can be divided into anatomical segments of the five lobes (the left upper lobe, the left lower lobe, the right upper lobe, the right middle lobe, and the right lower lobe). Further, each of the left lung and the right lung can be divided into anatomical segments of regions S1 to S8. The liver can be divided into anatomical segments of the left lobe and the right lobe or the regions S1 to S8. The kidneys can be divided into anatomical segments of the right and left regions. Some organs including the spleen are unable to be divided into anatomical segments. Such differences in the way of dividing into anatomical segments are referred to as differences in anatomical level. In the interpretation report, as the position of the region of interest, an anatomical region based on the various way of dividing is recorded. Therefore, the first analysis unit 22 acquires as a finding, anatomical level information included in the interpretation report and indicating the level of the anatomical segment of an organ in which the region of interest is present.

Natural language processing is a series of techniques for making computers process natural languages daily used by humans. Natural language processing allows segmentation of sentences into words, a syntactic analysis, a semantic analysis, and so on. The first analysis unit 22 segments a character string included in the interpretation report into words and makes a syntactic analysis by using a natural language processing technique and acquires findings. For example, when the finding remark included in the interpretation report says "A solid nodule measuring 1 cm in length and having a clear border is observed in the right upper lobe. This is suspected of being a lung adenocarcinoma", the first analysis unit 22 extracts words of "right upper lobe", "nodule", "clear border", "solid", "length", "1 cm", and "lung adenocarcinoma" as findings.

The first analysis unit 22 identifies from the acquired findings, an area of the human body about which the finding remark is made. The first analysis unit 22 identifies the type of disorder from the acquired findings. Specifically, the first analysis unit 22 identifies the disorder type and the disorder name as the type of disorder.

The first analysis unit 22 identifies the disorder type on the basis of the findings extracted from the interpretation report. For example, when "nodule" is included in the findings, the first analysis unit 22 identifies the disorder type as "nodular type". The disorder type of a tumor is a nodular type, and therefore, when "tumor" is included in the findings, the first analysis unit 22 identifies the disorder type as "nodular type". When the findings include, for example, "pneumonia" and "fatty liver", the first analysis unit 22 identifies the disorder type as "diffuse type". When the findings include, for example, "kidney enlargement" or "pancreatic duct dilatation", the first analysis unit 22 identifies the disorder type as "structural anomaly". In the present embodiment, the identified disorder type is also regarded as one of the findings.

The first analysis unit 22 identifies the disorder name on the basis of a finding corresponding to a disorder name from among the findings acquired from the interpretation report. For example, when "lung adenocarcinoma" is included in the findings, the first analysis unit 22 identifies the disorder name as "lung adenocarcinoma". When "interstitial pneumonia" is included in the findings, the first analysis unit 22 identifies the disorder name as "interstitial pneumonia". In the present embodiment, the identified disorder name is also regarded as one of the findings.

The findings include those related to a focal finding and those related to a nonfocal finding. The focal finding is a finding about a disorder occurring in a part of an organ, and examples thereof include a nodule, a tumor, a cyst, a calcification, and a calculus. The nonfocal finding is a finding about a disorder related to the entire organ, and examples thereof include organ-form-related findings such as enlargement, atrophy, and deforming and organ-specific findings such as interstitial pneumonia, lung emphysema, a fatty liver, hepatic cirrhosis, and pleural effusion.

The second analysis unit 23 derives medical image information from the medical image 52. Specifically, the second analysis unit 23 analyzes the medical image to thereby derive as medical image information, an image that includes a region of interest, such as a possible abnormal shadow, included in the medical image. For this, the second analysis unit 23 has a trained model (not illustrated) for which machine learning has been performed so as to detect a possible abnormal shadow in the medical image as a region of interest. In the present embodiment, the trained model is a convolutional neural network (CNN) for which deep learning has been performed by using training data so as to determine whether each of the pixels (voxels) of the medical image represents a possible abnormal shadow, and when being a possible abnormal shadow, identify the possible abnormal shadow as a region of interest.

The trained model is prepared, for example, on an organ-by-organ basis and has been trained so as to identify a region of interest that is a possible abnormal shadow and that is included in an organ. As the trained model, any trained model, such as a support vector machine (SVM), other than the convolutional neural network can be used.

Figure 6:
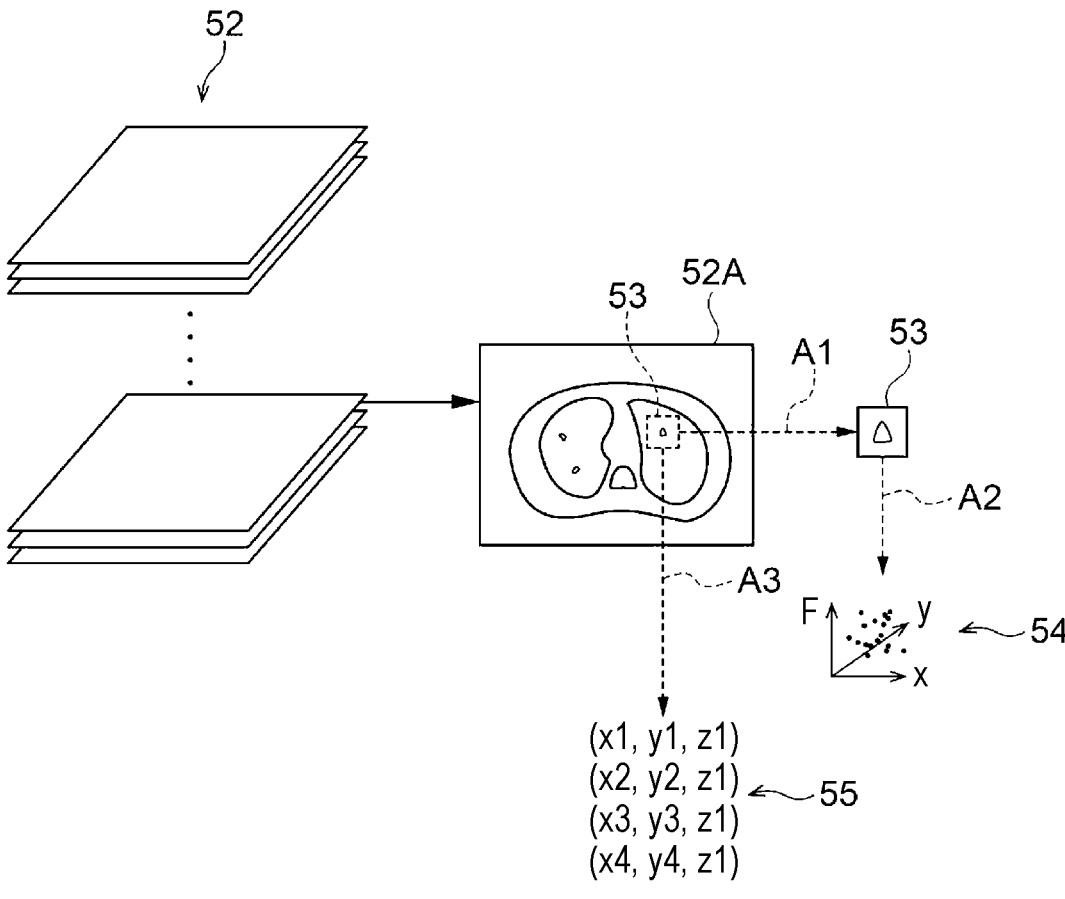
FIG. 6 is a diagram for explaining extraction of medical image information.

Among a plurality of tomographic images that constitute the medical image 52, from a tomographic image that includes a region of interest about which findings are recorded in the interpretation report 50, the second analysis unit 23 detects the region of interest. The second analysis unit 23 extracts from the tomographic image, an image (hereinafter referred to as "local image") of a local region that includes the detected region of interest as medical image information. FIG. 6 is a diagram for explaining extraction of medical image information. As illustrated in FIG. 6, the second analysis unit 23 identifies a tomographic image 52A associated with the interpretation report 50 and extracts from the tomographic image 52A, a local image 53 that includes a region of interest in the tomographic image 52A as medical image information as indicated by arrow A1. There may be a case where a plurality of regions of interest are extracted from one medical image. In this case, the second analysis unit 23 derives a plurality of local images 53 of the plurality of regions of interest respectively as medical image information.

Note that the second analysis unit 23 may derive feature values 54 of the local image 53 as medical image information as indicated by arrow A2. The feature values may be, for example, a set of vectors each having as its elements, the pixel position of a corresponding one of the pixels and the pixel value at the pixel position in the local image 53 or may be a set of vectors each having as its elements, a value obtained by performing a convolution process for the local image 53 by using a predetermined kernel and a position on the local image 53 corresponding to the value. In FIG. 6, the distribution of vectors each having as its elements, a corresponding pixel position on the local image 53 and a value F at the pixel position obtained as a result of convolution in a three-dimensional space when the plane of the local image 53 is regarded as the xy plane is illustrated as the feature values 54.

The second analysis unit 23 may use positional information 55 indicating the position of the local image 53 in the medical image 52 as medical image information as indicated by arrow A3. FIG. 6 illustrates the coordinate values (x1, y1, z1), (x2, y2, z1), (x3, y3, z1), and (x4, y4, z1) of the four corners of the local image 53 in the medical image 52 as positional information. In this case, the positional information also includes a link to the medical image 52. This link is a link to the medical image 52 saved on the image server 5.

The correspondence information deriving unit 24 derives correspondence information in which findings and medical image information about the region of interest are associated with each other. The derived correspondence information is put into a database format and registered in the management DB 7A.

The information management apparatus 20 of the management server 7 uses a large number of medical images and interpretation reports to acquire findings about a region of interest included in each of the medical images, and derives correspondence information in which the findings and medical image information about the region of interest are associated with each other. The information management apparatus 20 registers the derived correspondence information in the management DB 7A.

FIG. 7 is a diagram illustrating an example of the management DB 7A. As illustrated in FIG. 7, in the management DB 7A, a plurality of pieces of correspondence information derived from a plurality of combinations of medical images and interpretation reports are registered. Each piece of correspondence information includes an area, a disorder type, a disorder name, a plurality of disorder features, anatomical level information, size level information, medical image information, and finding remark generation information. In each piece of correspondence information, disorder features, anatomical level information, size level information, medical image information, and finding remark generation information are associated with each other on a per-area, per-disorder-type, or per-disorder-name basis. From a plurality of combinations of medical images and interpretation reports, a plurality of findings are acquired. Among the plurality of acquired findings, related findings, specifically disorder features, are included in one piece of correspondence information.

The area is an area based on findings acquired from an interpretation report by the first analysis unit 22. The disorder type and the disorder name are a disorder type and a disorder name based on the findings acquired from the interpretation report by the first analysis unit 22. The disorder features are the findings acquired from the interpretation report by the first analysis unit 22 as properties. Although FIG. 7 illustrates three disorder features for one disorder type or disorder name, the number of disorder features depends on the number of findings acquired from the interpretation report. The anatomical level information is information included in the interpretation report and indicating the level of an anatomical segment of an organ in which the region of interest is present. The size level information includes the direction of measurement of a size and information indicating whether the size is large or small, which are included in the interpretation report.

In correspondence information, a local image, in the medical image, related to the findings is included as the medical image information. In FIG. 7, a registered local image in the medical image is illustrated as a small square that represents the local image. As illustrated in FIG. 7, a plurality of pieces of medical image information may be included in one piece of correspondence information. As the medical image information, feature values derived from a local image may be included instead of or in addition to the local image. As the medical image information, a combination of a link to the medical image from which the correspondence information is acquired and positional information of a region of interest in the linked medical image may be included instead of the local image.

The finding remark generation information included in correspondence information is information indicating whether a template is used or natural language processing is used when a finding remark is generated with reference to the management DB 7A as described below. Specifically, as illustrated in FIG. 7, in the management DB 7A, <template> indicating that a finding remark is generated by using a template and <NLP> (natural language processing) indicating that a finding remark is generated by using natural language processing are recorded.

When the finding remark generation information indicates a template, for example, a template, such as "<feature 2> measuring <size> and associated with <feature 1> is observed in <location>." or "<feature 1> is observed in <location>", having blanks corresponding to findings registered in the correspondence information is saved on the management server 7. Upon generation of a finding remark at the interpretation WS 3 as described below, a template selected from among templates registered in the management DB 7A is acquired from the management server 7, findings are inserted into the blanks of the selected template, and a finding remark is generated. When the finding remark generation information indicates NLP, a finding remark is derived at the interpretation WS 3 described below by natural language processing.

Whether to set the finding remark generation information to a template or NLP depends on the number of findings to be included in the finding remark and is registered in the management DB 7A by an operator. Whether to set the finding remark generation information to a template or NLP may be determined in accordance with the area or the disorder. For example, regarding the lung, a relatively long finding remark tends to be recorded in the interpretation report, and therefore, when the area is the lung, NLP is recorded in the correspondence information.

Among the disorder names registered in the management DB 7A illustrated in FIG. 7, "post-operation" is the disorder name about a normal area. Disorder names other than "post-operation" are the disorder names about abnormal areas.

Figure 8:
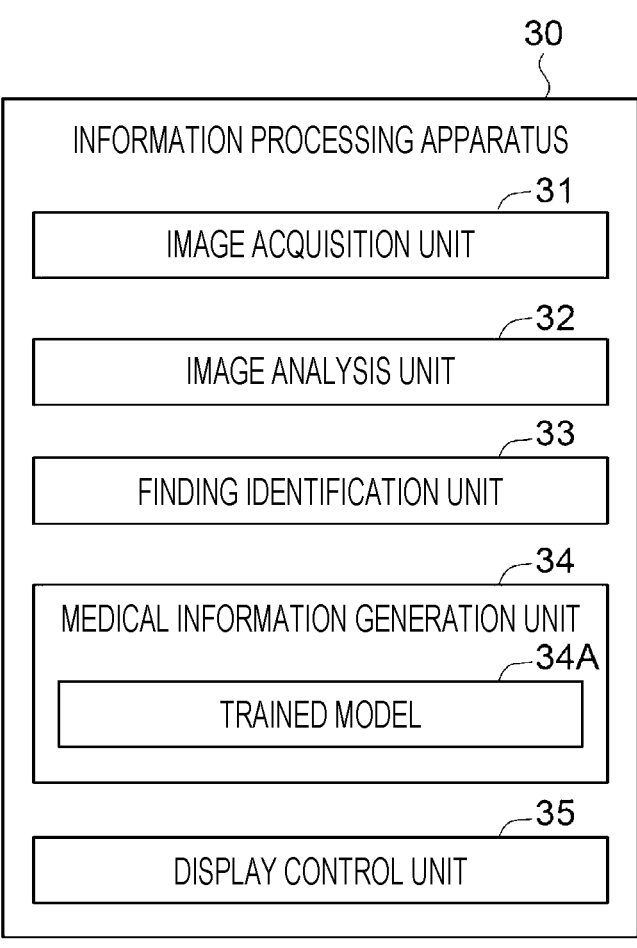
FIG. 8 is a block diagram illustrating an example functional configuration of the information processing apparatus according to the present embodiment.

Next, the functional configuration of the information processing apparatus according to the present embodiment will be described. FIG. 8 is a diagram illustrating the functional configuration of the information processing apparatus according to the present embodiment. As illustrated in FIG. 8, the information processing apparatus 30 includes an image acquisition unit 31, an image analysis unit 32, a finding identification unit 33, a medical information generation unit 34, and a display control unit 35. When the CPU 41 executes the information processing program 42, the CPU 41 functions as the image acquisition unit 31, the image analysis unit 32, the finding identification unit 33, the medical information generation unit 34, and the display control unit 35.

The image acquisition unit 31 acquires a medical image that is an interpretation target for creating an interpretation report, from the image server 5 in accordance with an instruction given by an interpreting doctor, who is an operator, using the input device 45. The medical image that is an interpretation target is referred to as a target medical image G0 in the following description.

The image analysis unit 32 analyzes the target medical image G0 to thereby identify a target region of interest, which is, for example, a possible abnormal shadow, included in the target medical image G0. For this, similarly to the second analysis unit 23 of the information management apparatus 20 according to the present embodiment, the image analysis unit 32 has a trained model (not illustrated) for which machine learning has been performed so as to discriminate a possible abnormal shadow in the medical image and detect the discriminated possible abnormal shadow as a target region of interest.

Figure 9:
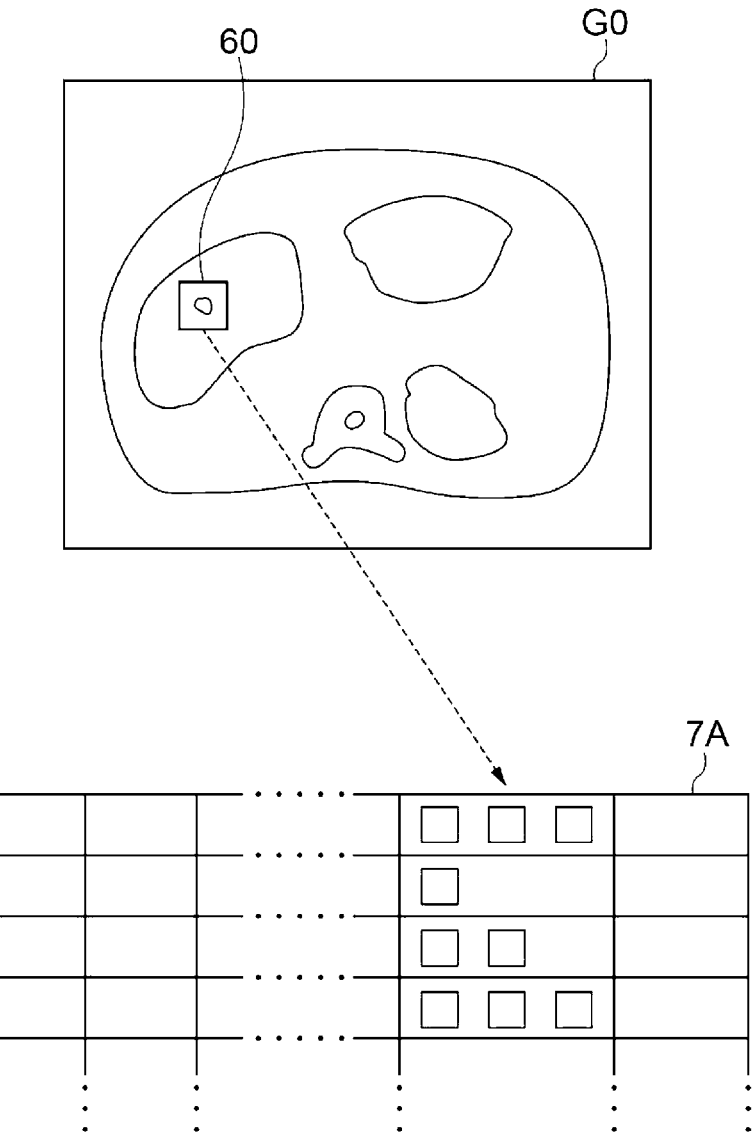
FIG. 9 is a diagram for explaining identification of findings.

The finding identification unit 33 identifies findings corresponding to medical image information that is about the target region of interest with reference to the management DB 7A. Note that the management DB 7A may be downloaded to the interpretation WS 3 and saved in the storage 43. FIG. 9 is a diagram for explaining identification of findings. As illustrated in FIG. 9, the finding identification unit 33 derives for a target region of interest 60 detected from the target medical image G0 by the image analysis unit 32, the degree of similarity between the target region of interest 60 and medical image information included in each of the plurality of pieces of correspondence information registered in the management DB 7A. When feature values are registered in the management DB 7A as medical image information, the finding identification unit 33 derives the feature values of the target region of interest 60 and derives the degree of similarity with the medical image information.

When positional information about a medical image and a link to the medical image are registered in the management DB 7A as medical image information, the finding identification unit 33 refers to the positional information registered in the management DB 7A and further refers to the medical image linked to the positional information to identify a region of interest in the medical image registered in the management DB 7A, and derives the degree of similarity between the region of interest and the target region of interest 60.

The finding identification unit 33 refers to a predetermined number of pieces of correspondence information having higher degrees of similarity in the management DB 7A and identifies findings. For example, when the predetermined number is three, the finding identification unit 33 refers to top three pieces of correspondence information having higher degrees of similarity and identifies first to third findings. For example, when a set of "ring-shaped deep dyeing" and "nodule", "angioma", and "cyst" are respectively registered as findings in top three pieces of correspondence information having higher degrees of similarity in the management DB 7A, the finding identification unit 33 identifies "ring-shaped deep dyeing" and "nodule" as the first finding, identifies "angioma" as the second finding, and identifies "cyst" as the third finding.

When an identified finding is related to a disorder, such as a nodule, a tumor, a cyst, a calcification, or a calculus, occurring in a part of an organ, the identified finding is a focal finding. In contrast, when an identified finding is related to the form of an organ, such as enlargement, atrophy, or deforming or related to a disorder specific to an organ, such as interstitial pneumonia, lung emphysema, a fatty liver, hepatic cirrhosis, or pleural effusion, the identified finding is a nonfocal finding.

The findings identified here are related to changes from a healthy state of the target region of interest. For example, finding items such as a nodule, a tumor, a cyst, a calcification, and a calculus that are included in focal findings described above are related to changes from a healthy state when a part of an organ is the region of interest. In contrast, findings such as interstitial pneumonia, lung emphysema, a fatty liver, hepatic cirrhosis, and pleural effusion that are included in nonfocal findings are related to changes from a healthy state when the entire organ is the region of interest.

The medical information generation unit 34 generates medical information that includes the identified findings. In the present embodiment, the medical information generation unit 34 generates as medical information, a finding remark that includes the identified findings. For this, the medical information generation unit 34 refers to finding remark generation information registered in correspondence information that includes the identified findings in the management DB 7A. The medical information generation unit 34 generates a finding remark with a generation method corresponding to the registered finding remark generation information. When the finding remark generation information indicates a template, the medical information generation unit 34 acquires a corresponding template from the management server 7 and inserts the identified findings into the blanks of the acquired template to thereby generate a finding remark.

For example, it is assumed that the template is "<feature 2> measuring <size> and associated with <feature 1> is observed in <location>". It is further assumed that the position of the region of interest identified by an image analysis is the right lung S5 and the size thereof is 2 cm. It is further assumed that the findings identified with reference to the management DB 7A are "ring-shaped deep dyeing" and "nodule". In this case, the medical information generation unit 34 generates a finding remark saying "<nodule> measuring <2 cm in size> and associated with <ring-shaped deep dyeing> is observed in <right lung S5>".

When the finding remark generation information indicates NLP, the medical information generation unit 34 generates a finding remark by natural language processing. For this, the medical information generation unit 34 has a trained model 34A for which machine learning has been performed so as to generate a finding remark from the result of analysis by the image analysis unit 32 and from the findings. As the trained model 34A, for example, a recurrent neural network can be used. To output a finding remark in response to input of the result of analysis by the image analysis unit 32 and the findings, the trained model 34A is built by making the recurrent neural network perform machine learning by using a large number of pieces of training data formed of combinations of results of analysis, findings, and finding remarks. When the finding remark generation information indicates NLP, the medical information generation unit 34 inputs the result of analysis by the image analysis unit 32 and the findings to the trained model 34A to make the trained model 34A output a finding remark, thereby generating the finding remark.

For example, when the result of analysis by the image analysis unit 32 include "left lung S6", "1.5 cm", and "3 mm" and the finding items are "length", "nodule", and "lung metastasis", the medical information generation unit 34 uses the trained model 34A to generate a finding remark such as "Nodules measuring 1.5 cm in length and 3 mm in length are observed in the left lung S6, which are suspected of being lung metastases".

In the present embodiment, in response to acquisition of the target medical image G0, the image analysis unit 32, the finding identification unit 33, and the medical information generation unit 34 perform the above-described processes and generate medical information. The medical information generated by the medical information generation unit 34 is saved in the storage 43 in association with the target region of interest identified in the target medical image G0.

Figure 10:
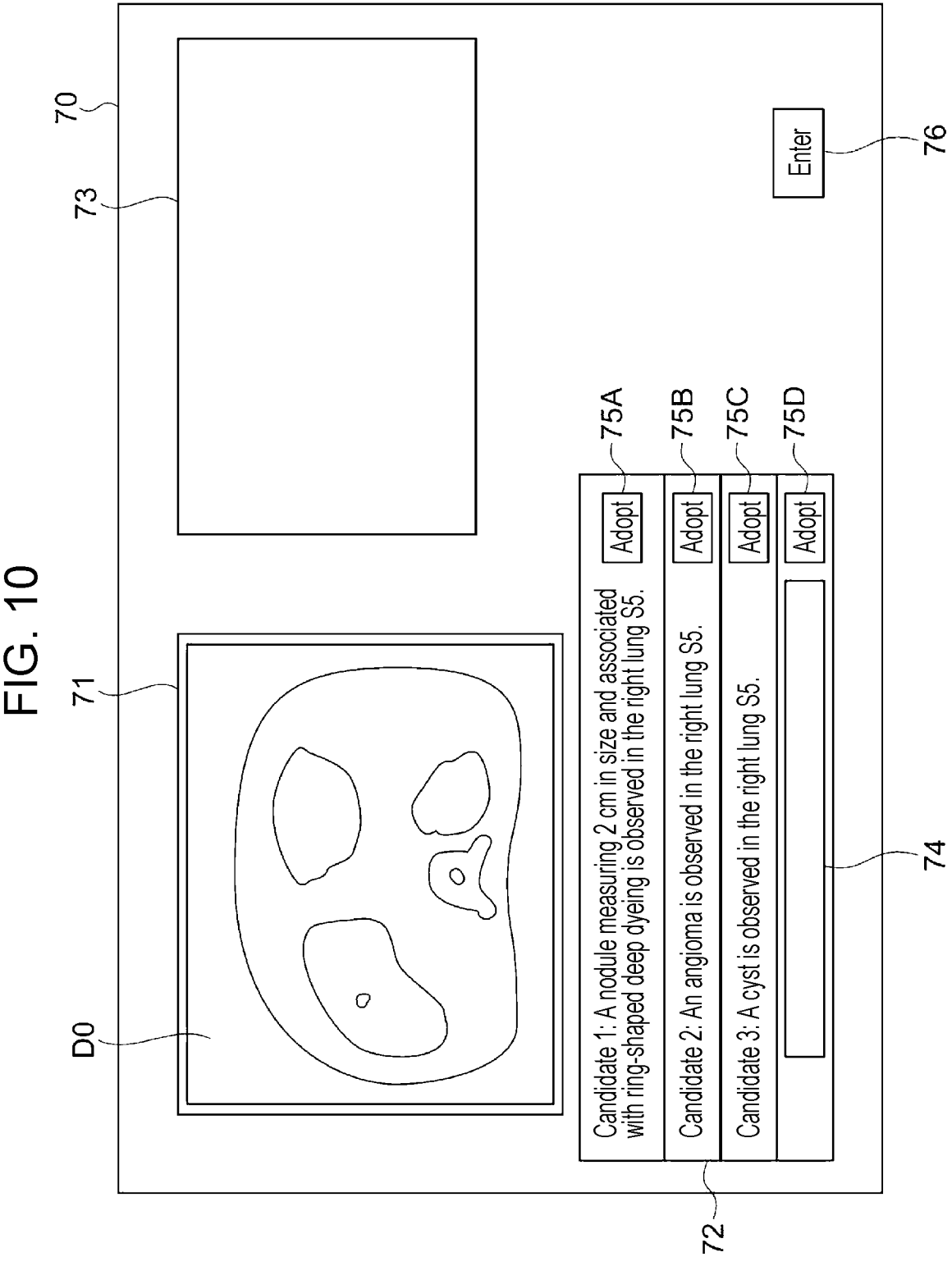
FIG. 10 is a diagram illustrating a display screen for medical information.

The display control unit 35 displays the medical information generated by the medical information generation unit 34. The present embodiment assumes that the medical information generation unit 34 derives a plurality of finding remarks as the medical information. Therefore, the display control unit 35 displays the plurality of finding remarks so as to be selectable. FIG. 10 is a diagram illustrating a display screen for medical information. As illustrated in FIG. 10, a display screen 70 includes an image display region 71, a candidate display region 72, and a text display region 73. In the image display region 71, a tomographic image, in the target medical image G0, that shows a cross section is displayed so as to be switchable.

As illustrated in FIG. 10, in a tomographic image D0 currently displayed in the image display region 71, a lesion is observed in the right lung. In response to clicking on the lesion by an interpreting doctor using the input device 45, a plurality of finding remarks generated by the medical information generation unit 34 are displayed in the candidate display region 72. In FIG. 10, three candidate finding remarks of candidate 1 to candidate 3 are displayed and an input box 74 is further displayed. To the right of the candidate finding remarks and the input box 74, adopt buttons 75A to 75D are displayed respectively.

When a finding remark that coincides with the result of interpretation of the lesion included in the tomographic image D0 is displayed in the candidate display region 72, the interpreting doctor selects the adopt button corresponding to the candidate finding remark. Accordingly, the selected finding remark is displayed in the text display region 73. On the other hand, when a finding remark that coincides with the result of interpretation of the lesion included in the tomographic image D0 is not displayed in the candidate display region 72, the interpreting doctor inputs a finding remark into the input box 74 by themselves and selects the adopt button 75D. Accordingly, the finding remark input into the input box 74 by the interpreting doctor is displayed in the text display region 73.

The interpreting doctor makes an interpretation while switching the tomographic image displayed in the image display region 71, clicks on a lesion position, makes candidate finding remarks be displayed in the candidate display region 72, and selects a finding remark repeatedly to thereby put a finding remark into the text display region 73.

In response to selection of an enter button 76 by the interpreting doctor, an interpretation report that includes the finding remark input into the text display region 73 is created. The created interpretation report is saved in the storage 43 together with the target medical image G0 and the result of detection of the region of interest. Thereafter, the created interpretation report is transferred to the report server 6 together with the target medical image G0 and the result of detection. On the report server 6, the transferred interpretation report is saved together with the target medical image G0 and the result of detection.

When the interpretation report is newly saved on the report server 6, the management server 7 may derive correspondence information as described above by using the new interpretation report and the medical image on which the new interpretation report has been created and update the management DB 7A by using the derived new correspondence information.

Figure 11:
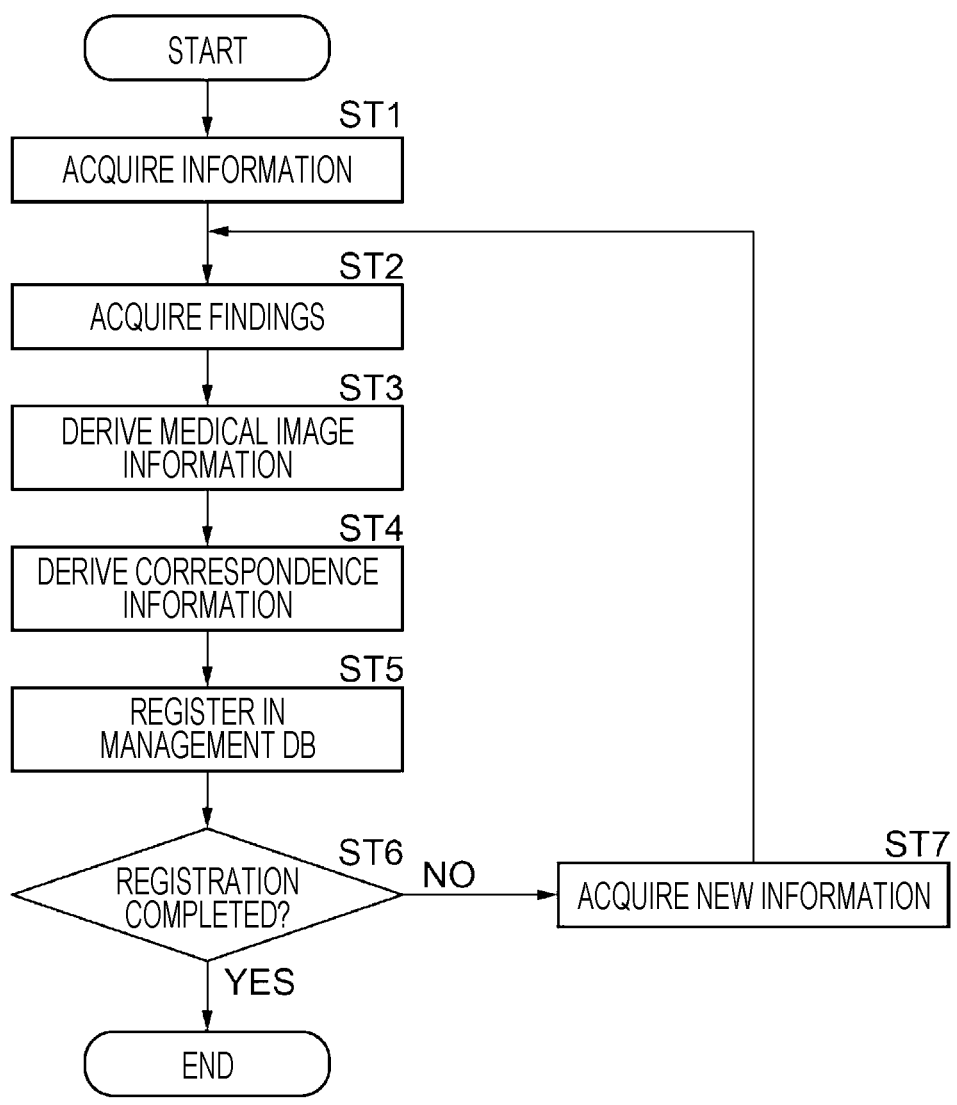
FIG. 11 is a flowchart illustrating an information management process performed in the present embodiment.

Next, an information management process performed in the present embodiment will be described. FIG. 11 is a flowchart illustrating the information management process performed in the present embodiment. In response to an instruction for a process start given by using the input device 15, the information acquisition unit 21 acquires a medical image and an interpretation report associated with the medical image from the image server 5 and the report server 6 respectively (information acquisition, step ST1). Next, the first analysis unit 22 analyzes the finding remark 51 included in the interpretation report 50 to thereby acquire findings about a region of interest included in the medical image 52 (step ST2). The second analysis unit 23 derives medical image information from the medical image 52 (step ST3).

Subsequently, the correspondence information deriving unit 24 derives correspondence information in which findings and the medical image information about the region of interest are associated with each other (step ST4). The correspondence information deriving unit 24 registers the derived correspondence information in the management DB 7A (step ST5). Next, determination as to whether registration of correspondence information about every interpretation report to be registered in the management DB 7A is completed is performed (step ST6). When the result of determination in step ST6 is negative, the information acquisition unit 21 acquires a new medical image and an interpretation report associated with the medical image from the image server 5 and the report server 6 respectively (new information acquisition, step ST7). The flow returns to step ST2, and the process in step ST2 and the subsequent steps is repeated. When the result of determination in step ST6 is positive, the process ends.

Figure 12:
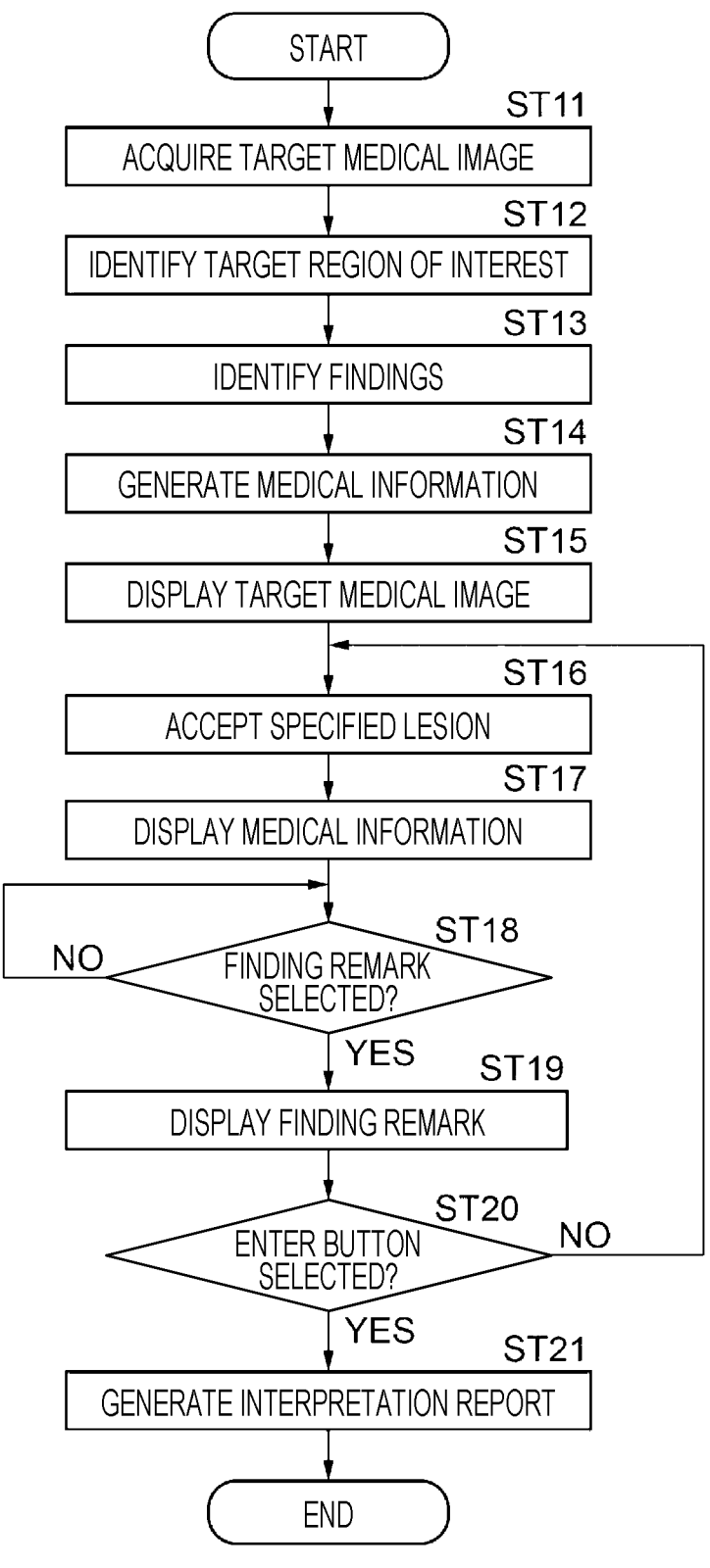
FIG. 12 is a flowchart illustrating information processing performed in the present embodiment.

Next, information processing performed in the present embodiment will be described. FIG. 12 is a flowchart illustrating the information processing performed in the present embodiment. In response to an instruction for creation of an interpretation report given by an interpreting doctor, the processing starts, and the image acquisition unit 31 acquires the target medical image G0 that is an interpretation target from the image server 5 (step ST11). The image analysis unit 32 analyzes the target medical image G0 to thereby identify a target region of interest, which is, for example, a possible abnormal shadow, included in the target medical image G0 (step ST12). Next, the finding identification unit 33 identifies findings corresponding to medical image information that is about the target region of interest with reference to the management DB 7A (step ST13). The medical information generation unit 34 generates medical information that includes the identified findings (step ST14). The generated medical information is saved in the storage 43.

Subsequently, the display control unit 35 displays the target medical image G0 on the display 44 (step ST15). The display control unit 35 further accepts a lesion, in the displayed target medical image G0, specified by the interpreting doctor (step ST16) and displays medical information derived for a corresponding region of interest corresponding to the specified lesion, that is, a plurality of finding remarks, in the candidate display region 72 of the display screen 70 (step ST17).

In response to selection of one finding remark from among the plurality of finding remarks displayed in the candidate display region 72 (positive in step ST18), the display control unit 35 displays the selected finding remark in the text display region 73 (step ST19). Determination as to whether the enter button 76 is selected is performed (step ST20), and when the result of determination in step ST20 is negative, the flow return to step ST16, and the process in step ST16 and the subsequent steps is repeated. When the result of determination in step ST20 is positive, an interpretation report is generated (step ST21), and the processing ends. The created interpretation report is saved in the storage 43 together with the target medical image G0 and the result of detection, and the created interpretation report is further transferred to the report server 6 together with the target medical image G0 and the result of detection.

As described above, in the present embodiment, findings about a region of interest included in a medical image are acquired, correspondence information in which the findings and medical image information about the region of interest are associated with each other is derived, and the correspondence information is registered in the management DB 7A. Therefore, a large number of medical images and findings on the medical images can be efficiently managed in the management DB 7A.

Specifically, a medical document, such as an interpretation report, associated with a medical image is acquired and findings about a region of interest included in the medical image are identified and acquired from the medical document, and accordingly, for the region of interest included in the medical image, the findings identified by an interpreting doctor can be acquired.

In the information processing apparatus according to the present embodiment, findings corresponding to medical image information that is about a target region of interest are identified with reference to the management DB 7A. Further, in the present embodiment, a finding remark that includes the findings is generated as medical information. Therefore, an interpretation report that includes the finding remark can be efficiently created. Further, a finding remark that does not depend on the interpreting doctor and that is uniform in quality can be generated.

Although correspondence information about each individual medical image is registered in the management DB 7A in the above-described embodiment, the present disclosure is not limited to this. Pieces of correspondence information about a plurality of related medical images may be put together in one set and registered in the management DB 7A. For example, as illustrated in FIG. 14, as correspondence information about the lung illustrated in the second row from the top, pieces of correspondence information about two medical images may be put together in one set and registered in the management DB 7A. In FIG. 14, the border between the pieces of correspondence information about two medical images put together in one set is represented by a dashed line. Regarding the pieces of correspondence information in the second row from the top in the management DB 7A illustrated in FIG. 14, the disorder type is the diffuse type for both of the two medical images, and the finding remark generation information indicates NLP for both of the two medical images. The disorder name is interstitial pneumonia for both of the two medical images, and the disorder feature 1 is ground-glass opacity for both of the two medical images. In contrast, the disorder features 2 and 3 are included only in the piece of correspondence information about the medical image in the upper row.

Examples of the plurality of related medical images include a plurality medical images of the same patient obtained at different times and medical images of the same patient, differing in modality. Examples of the plurality of medical images differing in modality include a combination of a CT image and an MRI image.

When the management DB 7A is thus derived, in the information processing apparatus according to the present embodiment, for example, for two related medical images, findings can be identified by referring to correspondence information that includes medical image information similar to both of the two medical images, with reference to the management DB 7A, and a finding remark on the two medical images can be generated.

Although a plurality of finding remarks are generated as medical information in the above-described embodiment, the present disclosure is not limited to this. One finding remark may be generated as medical information. In this case, the finding identification unit 33 may identify findings with reference to correspondence information having the highest degree of similarity in the management DB 7A, and the medical information generation unit 34 may generate a finding remark by using the identified findings.

Figure 13:
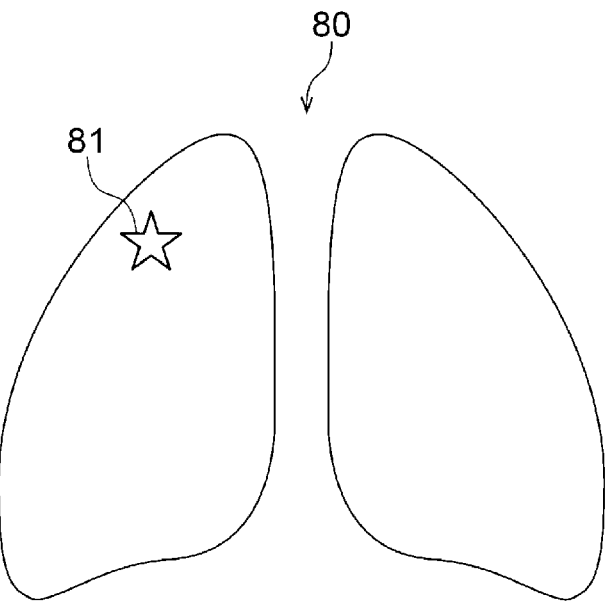
FIG. 13 is a diagram illustrating medical information that includes a graphical expression.

Although the medical information generation unit 34 derives a finding remark as medical information in the above-described embodiment, the present disclosure is not limited to this. The medical information generation unit 34 may derive medical information that includes a graphical expression of identified findings. FIG. 13 is a diagram illustrating example medical information that includes a graphical expression of identified finding items. It is assumed here that the identified findings are "right upper lobe" and "lung nodule". In this case, the medical information generation unit 34 may derive medical information in which a mark 81 is added to a schema 80 of the lung at the position of the right upper lobe as graphical information. Deriving and displaying medical information including such a graphical expression enables easy recognition of the position of the abnormal area.

Although the information processing apparatus 30 derives, in the above-described embodiment, medical information with reference to the management DB 7A generated by the information management apparatus of the present embodiment, the present disclosure is not limited to this. For example, correspondence information derived by associating findings and medical image information with each other by a manual operation may be registered in the management DB 7A, and with reference to the management DB 7A in which the correspondence information thus derived by the manual operation is registered, medical information may be derived.

Although medical information is generated in response to acquisition of the target medical image G0 in the above-described embodiment, the present disclosure is not limited to this. Each time the target medical image G0 is displayed and an interpreting doctor specifies an abnormal area on the displayed image, a finding remark about the specified abnormal area may be generated as medical information. In this case, the finding identification unit 33 identifies findings about the specified abnormal area, and the medical information generation unit 34 generates medical information about the specified abnormal area on the basis of the identified findings.

Although the information management apparatus includes the first analysis unit 22 and analyzes an interpretation report to thereby acquire findings in the above-described embodiment, the present disclosure is not limited to this. Findings may be acquired on the basis of input by an operator using the input device 15 or findings may be acquired by analyzing a medical image.

Processes performed by the first analysis unit 22 and the second analysis unit 23 of the information management apparatus 20 included in the management server 7 in the above-described embodiment may be performed by, for example, an external apparatus, such as another analysis server, connected to the network 10. In this case, the external apparatus acquires an interpretation report from the report server 6 and analyzes the interpretation report to thereby acquire findings, and transmits the findings to the management server 7. The external apparatus derives medical image information from a medical image associated with the interpretation report and transmits the derived medical image information to the management server 7. The information management apparatus 20 in the management server 7 derives correspondence information by using the findings and the medical image information derived by the external apparatus and registers the derived correspondence information in the management DB 7A.

In the above-described embodiment, the hardware configuration of the processing units, such as the information acquisition unit 21, the first analysis unit 22, the second analysis unit 23, and the correspondence information deriving unit 24 of the information management apparatus 20 and the image acquisition unit 31, the image analysis unit 32, the finding identification unit 33, the medical information generation unit 34, and the display control unit 35 of the information processing apparatus 30, that perform various types of processing is implemented as various processors as described below. The various processors include, in addition to a CPU, which is a general-purpose processor executing software (program) to function as various processing units as described above, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or a combination of two or more processors of the same type or different types (for example, a combination of a plurality of FPGAs or a combination of a CPU and an FPGA). Further, a plurality of processing units may be configured as one processor. As the first example of configuring a plurality of processing units as one processor, a form is possible where one or more CPUs and software are combined to configure one processor, and the processor functions as the plurality of processing units, representative examples of which include computers, such as a client and a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, as the hardware configuration of the various processors, more specifically, an electric circuit (circuitry) in which circuit elements, such as semiconductor elements, are combined can be used.

What is claimed is:

1. An information management apparatus comprising:
at least one processor,
the processor being configured to
acquire a medical image and a medical document associated with the medical image,
analyze a finding remark in the medical document to acquire at least one finding about at least one region of interest included in the medical image,
derive correspondence information in which the at least one finding and medical image information about the region of interest are associated with each other, register the correspondence information in a database,
display the medical image on a display, and
in response to the region of interest in the medical image being selected by a user, retrieve the at least one finding included in the correspondence information according to the region of interest from the database and display the at least one finding along with the medical image on the display,
wherein when the region of interest includes an abnormal area, the processor derives correspondence information in which the finding and the medical image information are associated with each other on a per-type-of-abnormal-area basis.

2. The information management apparatus according to claim 1, wherein the processor is configured to acquire findings, each of which is the finding, from a plurality of medical images respectively, and
derive the correspondence information in which each of the findings and a related one of pieces of medical image information, each of which is the medical image information, are associated with each other.

3. The information management apparatus according to claim 1, wherein the medical image information includes a local image of the region of interest in the medical image.

4. The information management apparatus according to claim 1, wherein the medical image information includes a feature value that indicates a feature of the region of interest in the medical image.

5. The information management apparatus according to claim 1, wherein the medical image information includes the medical image and positional information that indicates a position of the region of interest in the medical image.

6. The information management apparatus according to claim 1, wherein the processor is further configured to, when the region of interest includes a normal area, derive correspondence information in which the finding and the medical image information are associated with each other on a per-type-of-normal-area basis.

7. The information management apparatus according to claim 1, wherein the finding includes a property of the region of interest.

8. The information management apparatus according to claim 1, wherein the finding includes anatomical level information that indicates a level of an anatomical segment of an organ that includes the region of interest.

9. The information management apparatus according to claim 1, wherein the finding includes size information that indicates at least one of a direction of measurement or a size level of a size of the region of interest.

10. The information management apparatus according to claim 1, wherein the finding includes at least one of a focal finding or a nonfocal finding.

11. The information management apparatus according to claim 1, wherein the processor is configured to derive the correspondence information in which the finding and a generation method for medical information that includes the finding are further associated with each other.

12. The information management apparatus according to claim 1, wherein the processor analyzes the finding remark in the medical document by using a natural language processing method to acquire the at least one finding about the at least one region of interest included in the medical image.

13. An information processing apparatus comprising:

at least one processor, the processor being configured to acquire a target medical image that is a generation target of medical information, identify a target region of interest included in the target medical image, identify a finding corresponding to medical image information that is about the target region of interest retrieved from a database in which a plurality of pieces of correspondence information in each of which a finding and medical image information about a region of interest among various regions of interest included in a medical image among various medical images are associated with each other are registered, display the target medical image on a display, in response to the target region of the interest in the target medical image selected by a user, displaying a finding remark corresponding to the finding corresponding to the medical image information on the display along with the target medical image, and generate a medical document comprising the finding remark and associate the medical document with the target medical image, wherein when the target region of interest includes an abnormal area, the processor derives correspondence information in which the finding and the medical image information are associated with each other on a per-type-of-abnormal-area basis.

14. The information processing apparatus according to claim 13, wherein the database is created by registering correspondence information derived by the information management apparatus according to claim 1.

15. The information processing apparatus according to claim 13, wherein the processor is configured to identify the finding that is related to a change from a healthy state of the target region of interest, with reference to the correspondence information.

16. The information processing apparatus according to claim 13, wherein the processor is configured to further generate medical information that includes the identified finding.

17. The information processing apparatus according to claim 16, wherein the correspondence information is information in which the finding and a generation method for medical information that includes the finding are associated with each other, and the processor is configured to identify a generation method for the medical information about the target region of interest with reference to the database, and derive the medical information that includes the identified finding on the basis of the identified generation method.

18. A non-transitory computer-readable storage medium that stores an information management program causing a computer to perform:

a procedure of acquiring a medical image and a medical document associated with the medical image, a procedure of analyzing a finding remark in the medical document to acquire at least one finding about at least one region of interest included in the medical image, a procedure of deriving correspondence information in which the at least one finding and medical image information about the region of interest are associated with each other, a procedure of registering the correspondence information in a database, a procedure of displaying the medical image on the display, and a procedure of, in response to the region of interest in the medical image being selected by a user, retrieving the at least one finding included in the correspondence information according to the region of interest from the database and displaying the at least one finding along with the medical image on the display, wherein when the region of interest includes an abnormal area, correspondence information in which the finding and the medical image information are associated with each other is derived on a per-type-of-abnormal-area basis.

19. A non-transitory computer-readable storage medium that stores an information processing program causing a computer to perform:

a procedure of acquiring a target medical image that is a generation target of medical information, a procedure of identifying a target region of interest included in the target medical image, a procedure of identifying a finding corresponding to medical image information that is about the target region of interest retrieved from a database in which a plurality of pieces of correspondence information in each of which a finding and medical image information about a region of interest among various regions of interest included in a medical image among various medical images are associated with each other are registered, a procedure of displaying the target medical image on the display, a procedure of, in response to the target region of the interest in the target medical image selected by a user, displaying a finding remark corresponding to the finding corresponding to the medical image information on the display along with the target medical image, and a procedure of generating a medical document comprising the finding remark and associating the medical document with the target medical image, wherein when the target region of interest includes an abnormal area, correspondence information in which the finding and the medical image information are associated with each other is derived on a per-type-of-abnormal-area basis.

\* \* \* \* \*